US011832877B2

(12) United States Patent
Gwerder et al.

(10) Patent No.: US 11,832,877 B2
(45) Date of Patent: Dec. 5, 2023

(54) ELECTROSURGICAL ACCESS SHEATH

(71) Applicant: BRONCUS MEDICAL INC., San Jose, CA (US)

(72) Inventors: Eric Gwerder, San Jose, CA (US); Thomas M Keast, Sunnyvale, CA (US); Henky Wibowo, San Jose, CA (US)

(73) Assignee: BRONCUS MEDICAL INC., San Jose, CA (US)

( * ) Notice: Subject to any disclaimer, the term of this patent is extended or adjusted under 35 U.S.C. 154(b) by 742 days.

(21) Appl. No.: 16/496,425

(22) PCT Filed: Apr. 2, 2018

(86) PCT No.: PCT/US2018/025756
§ 371 (c)(1),
(2) Date: Sep. 21, 2019

(87) PCT Pub. No.: WO2018/187244
PCT Pub. Date: Oct. 11, 2018

(65) Prior Publication Data
US 2021/0106381 A1   Apr. 15, 2021

Related U.S. Application Data

(60) Provisional application No. 62/480,539, filed on Apr. 3, 2017.

(51) Int. Cl.
*A61B 18/14* (2006.01)
*A61B 90/00* (2016.01)
*A61B 18/00* (2006.01)

(52) U.S. Cl.
CPC .......... *A61B 18/1492* (2013.01); *A61B 90/37* (2016.02); *A61B 2018/00077* (2013.01);
(Continued)

(58) Field of Classification Search
CPC ...... A61B 18/1492; A61B 2018/00077; A61B 2018/00541; A61B 2018/00601; A61B 2018/141; A61B 90/37; A61B 2090/376
See application file for complete search history.

(56) References Cited

U.S. PATENT DOCUMENTS

| 3,433,226 A | 3/1969 | Boyd |
| 3,556,079 A | 1/1971 | Omizo |

(Continued)

FOREIGN PATENT DOCUMENTS

| DE | 3821836 A1 | 1/1990 |
| EP | 0347098 A2 | 12/1989 |

(Continued)

OTHER PUBLICATIONS

PCT Repub and International Search Report for WO2018087244, dated Aug. 13, 2018.
Supp EPO Search Report EP18780854 dated Mar. 12, 2021.

*Primary Examiner* — Michael F Peffley
*Assistant Examiner* — Bo Ouyang
(74) *Attorney, Agent, or Firm* — Batt IP A Law Corporation; Richard Batt

(57) ABSTRACT

An electrosurgical access catheter for assisting a physician perform an ancillary surgical procedure on a region of interest (ROI) in a patient has a tubular shaped elongate shaft and a ring-shaped active electrode located at the distal end. A passageway extends from the proximal section to the distal end of the shaft, and through the ring-shaped active electrode. The proximal section of the elongate shaft is detachably coupled to an electrosurgical controller such that the ring-shaped active electrode is operable with the electrosurgical controller and a dispersive electrode to electrosurgically make a circular-shaped incision through a tissue wall, carving a cylindrical-shaped tissue plug as the ring-shaped active electrode is advanced through the wall. The (Continued)

access sheath is advanced through the surgically created opening and without further dilation of the opening. The invention has particular applicability to the lung, and minimally invasive bronchoscopic procedures. Related methods are also described.

9 Claims, 15 Drawing Sheets

(52) U.S. Cl.
CPC ............... *A61B 2018/00541* (2013.01); *A61B 2018/00601* (2013.01); *A61B 2018/141* (2013.01); *A61B 2090/376* (2016.02)

(56) References Cited

U.S. PATENT DOCUMENTS

| | | |
|---|---|---|
| 3,565,062 A | 2/1971 | Kuris |
| 3,779,234 A | 12/1973 | Eggleton et al. |
| 3,823,717 A | 7/1974 | Pohlman et al. |
| 3,942,530 A | 3/1976 | Northeved |
| 4,249,539 A | 2/1981 | Vilkomerson et al. |
| 4,249,541 A | 2/1981 | Pratt |
| 4,319,580 A | 3/1982 | Colley et al. |
| 4,407,294 A | 10/1983 | Vilkomerson |
| 4,431,006 A | 2/1984 | Trimmer et al. |
| 4,538,618 A | 9/1985 | Rosenberg et al. |
| 4,582,067 A | 4/1986 | Silverstein et al. |
| 4,658,817 A | 4/1987 | Hardy |
| 4,674,498 A | 6/1987 | Stasz |
| 4,682,596 A | 7/1987 | Bales et al. |
| 4,750,902 A | 6/1988 | Wuchinich et al. |
| 4,757,821 A | 7/1988 | Snyder |
| 4,757,822 A | 7/1988 | Giuliomaria et al. |
| 4,769,031 A | 9/1988 | McGough et al. |
| 4,770,185 A | 9/1988 | Silverstein et al. |
| 4,771,788 A | 9/1988 | Millar |
| 4,773,413 A | 9/1988 | Hussein et al. |
| 4,785,402 A | 11/1988 | Matsuo et al. |
| 4,802,476 A | 2/1989 | Noerenberg et al. |
| 4,807,634 A | 2/1989 | Enjoji et al. |
| 4,808,153 A | 2/1989 | Parisi |
| 4,834,102 A | 5/1989 | Schwarzchild et al. |
| 4,869,268 A | 9/1989 | Yoon |
| 4,870,953 A | 10/1989 | DonMicheal et al. |
| 4,887,606 A | 12/1989 | Yock et al. |
| 4,899,757 A | 2/1990 | Pope, Jr. et al. |
| 4,917,097 A | 4/1990 | Proudian et al. |
| 4,920,954 A | 5/1990 | Alliger et al. |
| 4,924,863 A | 5/1990 | Sterzer |
| 4,936,281 A | 6/1990 | Stasz |
| 4,967,753 A | 11/1990 | Haase et al. |
| 4,977,898 A | 12/1990 | Schwarzschild et al. |
| 5,002,058 A | 3/1991 | Martinelli |
| 5,030,201 A | 7/1991 | Palestrant |
| 5,069,664 A | 12/1991 | Guess et al. |
| 5,081,993 A | 1/1992 | Kitney et al. |
| 5,100,423 A | 3/1992 | Fearnot |
| 5,105,816 A | 4/1992 | Shimura et al. |
| 5,105,817 A | 4/1992 | Uchibori et al. |
| 5,125,926 A | 6/1992 | Rudko et al. |
| 5,127,917 A | 7/1992 | Niederhauser et al. |
| 5,131,394 A | 7/1992 | Gehlbach |
| 5,148,809 A | 9/1992 | Biegeleisen-Knight et al. |
| 5,170,793 A | 12/1992 | Takano et al. |
| 5,190,528 A | 3/1993 | Fonger et al. |
| 5,201,316 A | 4/1993 | Pomeranz et al. |
| 5,209,721 A | 5/1993 | Wilk |
| 5,226,421 A | 7/1993 | Frisbie et al. |
| 5,254,112 A | 10/1993 | Sinofsky et al. |
| 5,257,990 A | 11/1993 | Nash |
| 5,259,385 A | 11/1993 | Miller et al. |
| 5,261,409 A | 11/1993 | Dardel |
| 5,275,166 A | 1/1994 | Vaitekunas et al. |
| 5,295,484 A | 3/1994 | Marcus et al. |
| 5,299,578 A | 4/1994 | Rotteveel et al. |
| 5,309,915 A | 5/1994 | Ember |
| 5,311,871 A | 5/1994 | Yock |
| 5,313,950 A | 5/1994 | Ishikawa et al. |
| 5,316,001 A | 5/1994 | Ferek-Petric et al. |
| 5,320,106 A | 6/1994 | Tanaka |
| 5,334,183 A | 8/1994 | Wuchinich |
| 5,339,289 A | 8/1994 | Erickson |
| 5,344,420 A | 9/1994 | Hilal et al. |
| 5,351,693 A | 10/1994 | Taimisto et al. |
| 5,363,852 A | 11/1994 | Sharkawy |
| 5,363,853 A | 11/1994 | Lieber et al. |
| 5,366,490 A | 11/1994 | Edwards et al. |
| 5,368,035 A | 11/1994 | Hamm et al. |
| 5,372,138 A | 12/1994 | Crowley et al. |
| 5,375,602 A | 12/1994 | Lancee et al. |
| 5,377,682 A | 1/1995 | Ueno et al. |
| 5,380,316 A | 1/1995 | Aita et al. |
| 5,381,795 A | 1/1995 | Nordgren et al. |
| 5,383,460 A | 1/1995 | Jang et al. |
| 5,385,148 A | 1/1995 | Lesh et al. |
| 5,389,096 A | 2/1995 | Aita et al. |
| 5,402,792 A | 4/1995 | Kimura |
| 5,409,012 A | 4/1995 | Sahatjian |
| 5,409,019 A | 4/1995 | Wilk |
| 5,411,466 A | 5/1995 | Hess |
| 5,427,107 A | 6/1995 | Milo et al. |
| 5,435,314 A | 7/1995 | Dias |
| 5,454,373 A | 10/1995 | Koger et al. |
| 5,454,809 A | 10/1995 | Janssen |
| 5,456,258 A | 10/1995 | Kondo et al. |
| 5,458,120 A | 10/1995 | Lorraine |
| 5,464,016 A | 11/1995 | Nicholas et al. |
| 5,465,726 A | 11/1995 | Dickinson et al. |
| 5,470,308 A | 11/1995 | Edwards et al. |
| 5,474,075 A | 12/1995 | Goldberg et al. |
| 5,484,416 A | 1/1996 | Gittings |
| 5,485,841 A | 1/1996 | Watkin et al. |
| 5,500,012 A | 3/1996 | Brucker et al. |
| 5,505,088 A | 4/1996 | Chandraratna et al. |
| 5,520,684 A | 5/1996 | Imran |
| 5,524,630 A | 6/1996 | Crowley |
| 5,527,292 A | 6/1996 | Adams et al. |
| 5,545,195 A | 8/1996 | Lennox et al. |
| 5,554,118 A | 9/1996 | Jang |
| 5,554,152 A | 9/1996 | Aita et al. |
| 5,555,886 A | 9/1996 | Weng et al. |
| 5,564,434 A | 10/1996 | Halperin et al. |
| 5,571,086 A | 11/1996 | Kaplan et al. |
| 5,571,180 A | 11/1996 | Blom |
| 5,573,531 A | 11/1996 | Gregory |
| 5,588,432 A | 12/1996 | Crowley |
| 5,596,989 A | 1/1997 | Morita |
| 5,599,344 A | 2/1997 | Paterson |
| 5,615,679 A | 4/1997 | Ri et al. |
| 5,630,837 A | 5/1997 | Crowley |
| D380,266 S | 6/1997 | Boatman et al. |
| 5,647,871 A | 7/1997 | Levine et al. |
| 5,658,279 A | 8/1997 | Nardella et al. |
| 5,658,280 A | 8/1997 | Issa |
| 5,672,172 A | 9/1997 | Zupkas |
| 5,678,555 A | 10/1997 | O'Connell |
| 5,704,361 A | 1/1998 | Seward et al. |
| 5,718,701 A | 2/1998 | Shai et al. |
| 5,736,642 A | 4/1998 | Yost et al. |
| 5,752,518 A | 5/1998 | McGee et al. |
| 5,755,769 A | 5/1998 | Richard et al. |
| 5,755,778 A | 5/1998 | Kleshinski |
| 5,759,769 A | 6/1998 | Sia et al. |
| 5,779,642 A | 7/1998 | Nightengale |
| 5,792,119 A | 8/1998 | Marx |
| 5,795,325 A | 8/1998 | Valley et al. |
| 5,810,008 A | 9/1998 | Dekel et al. |
| 5,830,222 A | 11/1998 | Makower |
| 5,840,431 A | 11/1998 | Kall |
| 5,843,019 A * | 12/1998 | Eggers ............... A61M 25/0133 606/41 |
| 5,855,597 A | 1/1999 | Jayaraman |

(56) References Cited

U.S. PATENT DOCUMENTS

| | | |
|---|---|---|
| 5,860,951 A | 1/1999 | Eggers et al. |
| 5,876,345 A | 3/1999 | Eaton et al. |
| 5,885,219 A | 3/1999 | Nightengale |
| 5,916,158 A | 6/1999 | Webster, Jr. |
| 5,921,995 A | 7/1999 | Kleshinski |
| 5,951,567 A | 9/1999 | Javier, Jr. et al. |
| 5,954,649 A | 9/1999 | Chia et al. |
| 5,957,849 A | 9/1999 | Munro |
| 5,957,919 A | 9/1999 | Laufer |
| 5,967,990 A | 10/1999 | Thierman et al. |
| 5,971,980 A | 10/1999 | Sherman |
| 5,984,871 A | 11/1999 | Tenhoff et al. |
| 5,993,484 A | 11/1999 | Shmulewitz |
| 6,002,955 A | 12/1999 | Willems et al. |
| 6,003,517 A | 12/1999 | Sheffield et al. |
| 6,004,269 A | 12/1999 | Crowley et al. |
| 6,004,273 A | 12/1999 | Sakamoto et al. |
| 6,004,319 A | 12/1999 | Goble et al. |
| 6,011,995 A | 1/2000 | Guglielmi et al. |
| 6,013,033 A | 1/2000 | Berger et al. |
| 6,015,405 A | 1/2000 | Schwartz et al. |
| 6,024,703 A | 2/2000 | Zanelli et al. |
| 6,032,674 A | 3/2000 | Eggers et al. |
| 6,045,511 A | 4/2000 | Ott et al. |
| 6,045,532 A | 4/2000 | Eggers et al. |
| 6,059,731 A | 5/2000 | Seward et al. |
| 6,064,902 A | 5/2000 | Haissaguerre et al. |
| 6,068,638 A | 5/2000 | Makower |
| 6,070,094 A | 5/2000 | Swanson et al. |
| 6,074,349 A | 6/2000 | Crowley |
| 6,080,109 A | 6/2000 | Baker et al. |
| 6,096,053 A | 8/2000 | Bates |
| 6,112,123 A | 8/2000 | Kelleher et al. |
| 6,117,101 A | 9/2000 | Diederich et al. |
| 6,129,726 A | 10/2000 | Edwards et al. |
| 6,143,019 A | 11/2000 | Motamedi et al. |
| 6,159,225 A | 12/2000 | Makower |
| 6,165,127 A | 12/2000 | Crowley |
| 6,174,323 B1 | 1/2001 | Biggs et al. |
| 6,183,444 B1 | 2/2001 | Glines et al. |
| 6,190,353 B1 | 2/2001 | Makower et al. |
| 6,200,313 B1 | 3/2001 | Abe et al. |
| 6,206,831 B1 | 3/2001 | Suorsa et al. |
| 6,235,024 B1 | 5/2001 | Tu |
| 6,241,742 B1 | 6/2001 | Spence et al. |
| 6,245,020 B1 | 6/2001 | Moore et al. |
| 6,245,066 B1 * | 6/2001 | Morgan .............. A61B 18/1485 606/41 |
| 6,258,100 B1 | 7/2001 | Alferness et al. |
| 6,283,951 B1 | 9/2001 | Christopher et al. |
| 6,283,983 B1 | 9/2001 | Makower et al. |
| 6,287,290 B1 | 9/2001 | Perkins et al. |
| 6,293,951 B1 | 9/2001 | Alferness et al. |
| 6,309,375 B1 | 10/2001 | Glines et al. |
| 6,336,933 B1 | 1/2002 | Parodi |
| 6,394,956 B1 | 5/2002 | Chandrasekaran et al. |
| 6,488,673 B1 | 12/2002 | Laufer et al. |
| 6,490,474 B1 | 12/2002 | Parker et al. |
| 6,514,249 B1 | 2/2003 | Maguire et al. |
| 6,514,290 B1 | 2/2003 | Loomas |
| 6,585,655 B2 | 7/2003 | Crowley |
| 6,599,311 B1 | 7/2003 | Biggs et al. |
| 6,623,437 B2 | 9/2003 | Hinchliffe et al. |
| 6,629,951 B2 | 10/2003 | Laufer et al. |
| 6,634,363 B1 | 10/2003 | Danek et al. |
| 6,692,494 B1 | 2/2004 | Cooper et al. |
| 6,712,804 B2 | 3/2004 | Roue et al. |
| 6,712,812 B2 | 3/2004 | Roschak et al. |
| 6,749,606 B2 | 6/2004 | Keast et al. |
| 6,770,070 B1 | 8/2004 | Balbierz |
| 6,970,733 B2 | 11/2005 | Parker et al. |
| 6,997,189 B2 | 2/2006 | Biggs et al. |
| 7,022,088 B2 | 4/2006 | Keast et al. |
| 7,175,644 B2 | 2/2007 | Cooper et al. |
| 7,393,330 B2 | 7/2008 | Keast et al. |
| 8,709,034 B2 | 4/2014 | Keast et al. |
| 8,784,400 B2 | 7/2014 | Roschak |
| 9,265,468 B2 | 2/2016 | Rai et al. |
| 2001/0007940 A1 | 7/2001 | Tu et al. |
| 2002/0022833 A1 | 2/2002 | Maguire et al. |
| 2002/0042564 A1 | 4/2002 | Cooper et al. |
| 2002/0042565 A1 | 4/2002 | Cooper et al. |
| 2002/0111619 A1 | 8/2002 | Keast et al. |
| 2002/0111620 A1 | 8/2002 | Cooper et al. |
| 2002/0128647 A1 | 9/2002 | Roschak et al. |
| 2003/0070676 A1 | 4/2003 | Cooper et al. |
| 2003/0130657 A1 | 7/2003 | Tom et al. |
| 2003/0195511 A1 * | 10/2003 | Barry ................ A61B 18/1492 606/45 |
| 2004/0073155 A1 | 4/2004 | Laufer et al. |
| 2004/0073201 A1 | 4/2004 | Cooper et al. |
| 2004/0211434 A1 | 10/2004 | Loomas et al. |
| 2004/0220556 A1 | 11/2004 | Cooper et al. |
| 2005/0043751 A1 | 2/2005 | Phan et al. |
| 2005/0043752 A1 | 2/2005 | Phan et al. |
| 2005/0049615 A1 | 3/2005 | Cooper et al. |
| 2005/0056292 A1 | 3/2005 | Cooper |
| 2005/0060041 A1 | 3/2005 | Phan et al. |
| 2005/0060042 A1 | 3/2005 | Phan et al. |
| 2005/0060044 A1 | 3/2005 | Roschak et al. |
| 2005/0085801 A1 | 4/2005 | Cooper et al. |
| 2005/0096529 A1 | 5/2005 | Cooper et al. |
| 2005/0107783 A1 | 5/2005 | Tom et al. |
| 2005/0119653 A1 * | 6/2005 | Swanson ............ A61B 18/1492 606/49 |
| 2005/0137518 A1 | 6/2005 | Biggs et al. |
| 2005/0137611 A1 | 6/2005 | Escudero et al. |
| 2005/0137712 A1 | 6/2005 | Biggs et al. |
| 2005/0137715 A1 | 6/2005 | Phan et al. |
| 2005/0171527 A1 | 8/2005 | Bhola |
| 2005/0177144 A1 | 8/2005 | Phan et al. |
| 2005/0182475 A1 | 8/2005 | Jen et al. |
| 2005/0192526 A1 | 9/2005 | Biggs et al. |
| 2006/0116749 A1 | 6/2006 | Willink et al. |
| 2006/0135984 A1 | 6/2006 | Kramer et al. |
| 2006/0142672 A1 | 6/2006 | Keast et al. |
| 2006/0276807 A1 | 12/2006 | Keast et al. |
| 2006/0280772 A1 | 12/2006 | Roschak et al. |
| 2006/0280773 A1 | 12/2006 | Roschak et al. |
| 2007/0066972 A1 * | 3/2007 | Ormsby ............ A61B 18/1492 606/41 |
| 2007/0093802 A1 | 4/2007 | Danek et al. |
| 2007/0123922 A1 | 5/2007 | Cooper et al. |
| 2008/0140073 A1 | 6/2008 | Schwartz |
| 2008/0249523 A1 | 10/2008 | McPherson et al. |
| 2008/0287803 A1 * | 11/2008 | Li ..................... A61B 8/445 382/128 |
| 2011/0184409 A1 | 7/2011 | Jenkins et al. |
| 2011/0190659 A1 | 8/2011 | Long et al. |
| 2011/0190755 A1 | 8/2011 | Mathur et al. |
| 2012/0172714 A1 | 7/2012 | Govari et al. |
| 2012/0197246 A1 * | 8/2012 | Mauch ............... A61B 18/1492 606/41 |
| 2013/0041373 A1 | 2/2013 | Laufer |
| 2013/0123638 A1 | 5/2013 | Tom et al. |
| 2015/0174427 A1 | 6/2015 | Amthor et al. |
| 2015/0305807 A1 | 10/2015 | Kelly et al. |
| 2016/0158490 A1 | 6/2016 | Leeflang et al. |
| 2017/0245740 A1 * | 8/2017 | Krimsky ............ A61B 1/00128 |

FOREIGN PATENT DOCUMENTS

| | | |
|---|---|---|
| EP | 0443256 A1 | 8/1991 |
| JP | 2000107178 A | 4/2000 |
| JP | 2001104315 B | 11/2009 |
| WO | 8906515 A1 | 7/1989 |
| WO | 9001300 A1 | 2/1990 |
| WO | 9502361 A1 | 1/1995 |
| WO | 9639914 A1 | 12/1996 |
| WO | 9717014 A1 | 5/1997 |
| WO | 9717105 A1 | 5/1997 |
| WO | 9816161 A1 | 4/1998 |
| WO | 9828035 A1 | 7/1998 |

(56) References Cited

FOREIGN PATENT DOCUMENTS

| WO | 9901076 A1 | 1/1999 |
|---|---|---|
| WO | 9911182 A1 | 3/1999 |
| WO | 9925419 A1 | 5/1999 |
| WO | 9960953 A1 | 12/1999 |
| WO | 0067825 A1 | 11/2000 |
| WO | 0072908 A1 | 12/2000 |
| WO | 0132088 A2 | 5/2001 |
| WO | 0200278 A2 | 1/2002 |
| WO | 2003020136 A1 | 3/2003 |

* cited by examiner

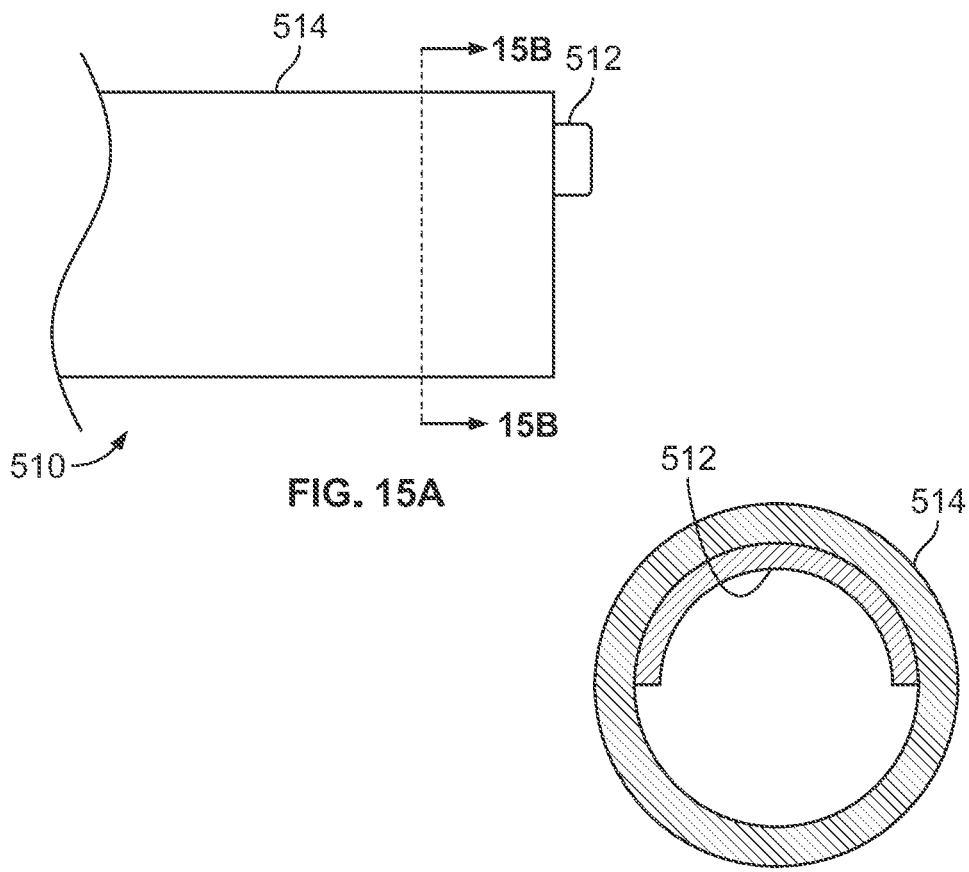
FIG. 15A
FIG. 15B
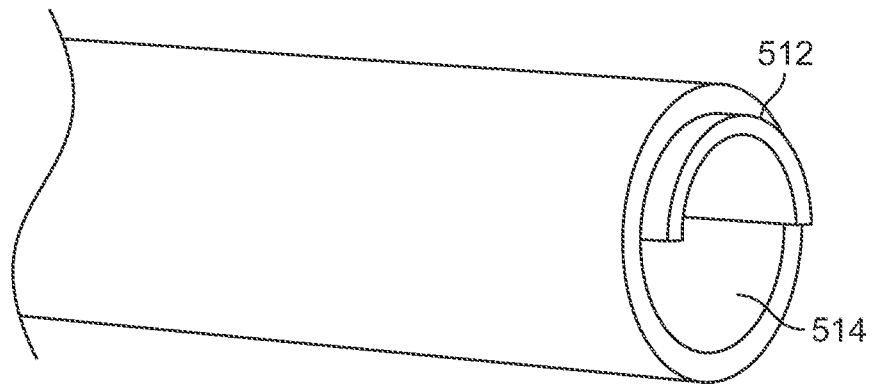
FIG. 15C

ELECTROSURGICAL ACCESS SHEATH

CROSS-REFERENCE TO RELATED APPLICATIONS

This application claims priority to provisional patent application No. 62/480,539, filed Apr. 3, 2017, and entitled "ELECTROSURGICAL ACCESS SHEATH".

BACKGROUND OF THE INVENTION

The invention relates to surgical instruments, and more particularly, to bronchoscopic access catheters having electrosurgical functionality to cut lung tissue.

In various medical procedures, access catheters are advanced through the natural lumens of the body and to a target tissue site where a medical procedure is carried out. The access catheter serves to prevent collateral damage to tissue as surgical tools are advanced from outside the body to the target site, and in the case of tumor biopsy and cancer treatments, the access catheter potentially prevents spreading of cancer cells as the biopsy sample is collected and withdrawn from the body.

The access catheters must be large enough to accommodate the tools which are to be passed through the access catheter. The relatively large size of the access catheter necessary to accommodate the tools, however, prohibits the access catheter from reaching smaller more remote target areas without damaging the tissue. Consequently, dilation and expansion of tissues is required in order to advance the access catheter into position. Additional tools and instruments are required to safely dilate tissue spaces, and to advance the access catheter into position. Undesirably, in some cases, multiple steps and tool exchanges may be required involving inflatable balloons, and dilating instruments.

Notwithstanding the above, an apparatus and related method that overcomes the above mentioned challenges is desirable.

SUMMARY OF THE INVENTION

An electrosurgical access sheath system and method enables a physician to reach target regions of interest exterior to the airways in the lung of a patient.

In embodiments, the access sheath creates large incisions using radio frequency (RF) energy. After an opening is created using the RF energy, the access sheath may be advanced through the opening without dilating the opening. In embodiments, the radio frequency energy is monopolar-based based.

In embodiments, the distal working section of the access sheath through the opening has a constant diameter.

In embodiments, subsequent to placing the access sheath in position, various medical procedures are performed through the access sheath including diagnostic and treatment procedures. In embodiments, tissue biopsy or electrosurgical ablation is performed on suspect growths.

Still other descriptions, objects and advantages of the present invention will become apparent from the detailed description to follow, together with the accompanying drawings.

BRIEF DESCRIPTION OF THE DRAWINGS

FIGS. 15A, 15B are partial side and end views respectively of another electrosurgical access sheath.

FIG. 15C is a partial perspective view of the electrosurgical access sheath shown in FIGS. 15A, 15B.

DETAILED DESCRIPTION OF THE INVENTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

The following patents and applications are incorporated herein by reference in their entirety: U.S. Pat. Nos. 6,692,494, 8,709,034, 8,784,400, 7,393,330, and 9,265,468 and US Patent Publication No. 2013/0123638.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Figure 1A:
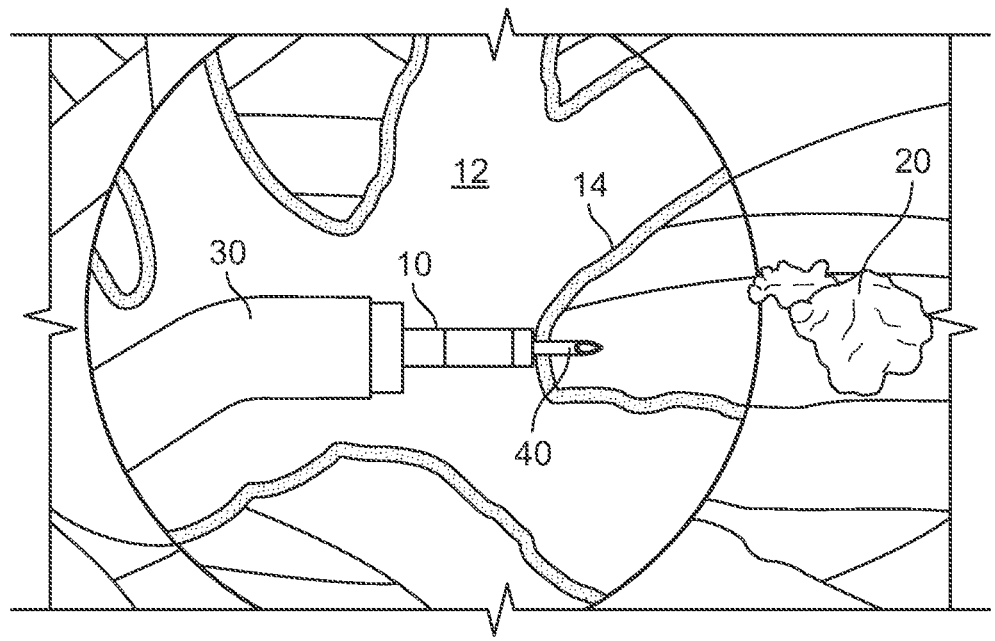
FIGS. 1A-1C sequentially illustrate a bronchoscopic-based technique for advancing an access sheath from within a lung airway to a region of interest located outside of the airway in the lung parenchyma.
Figure 1B:
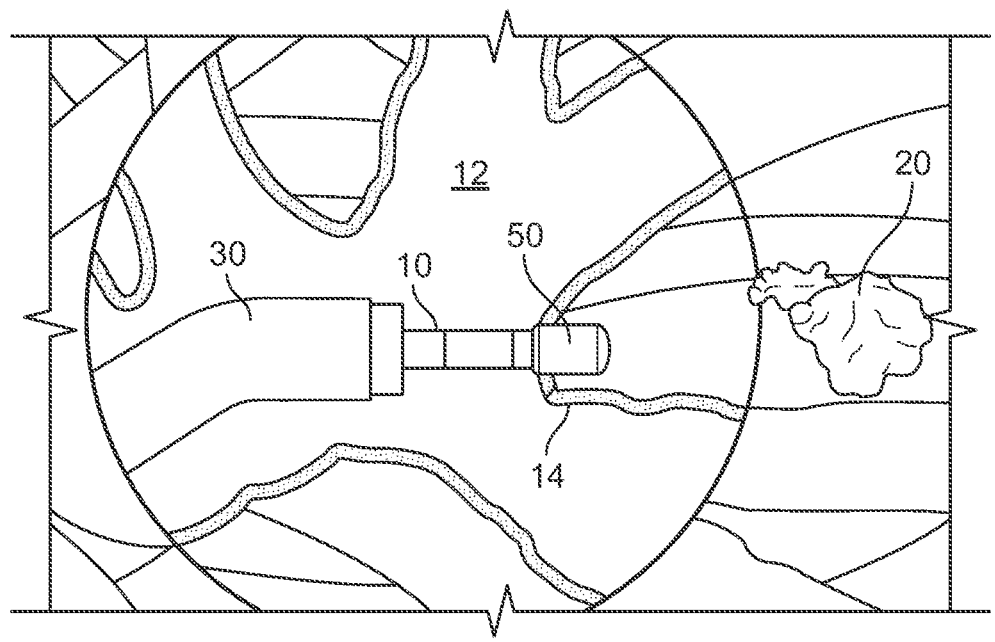
Figure 1C:
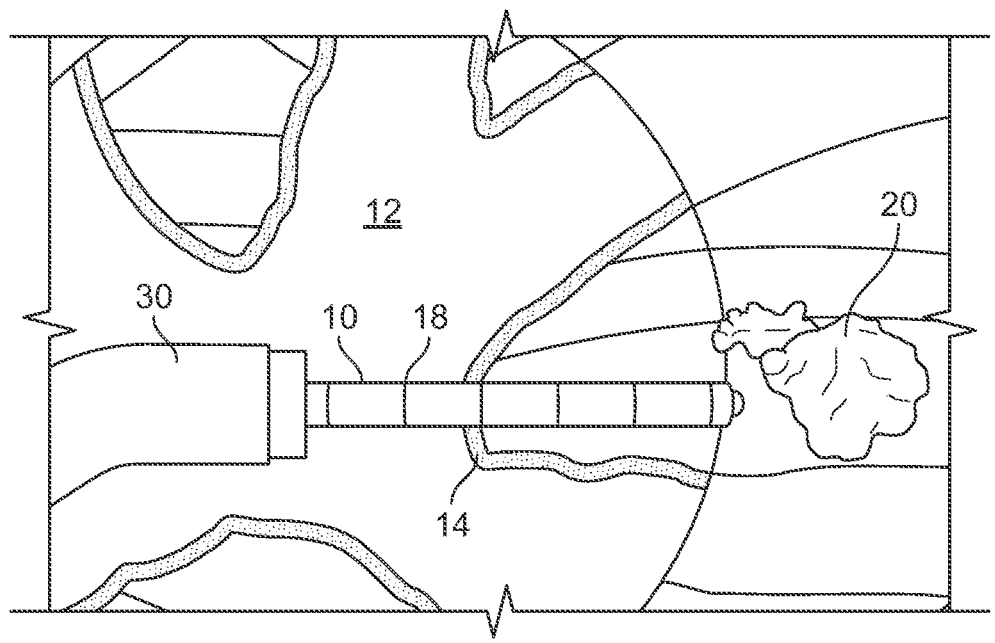
Figure 2:
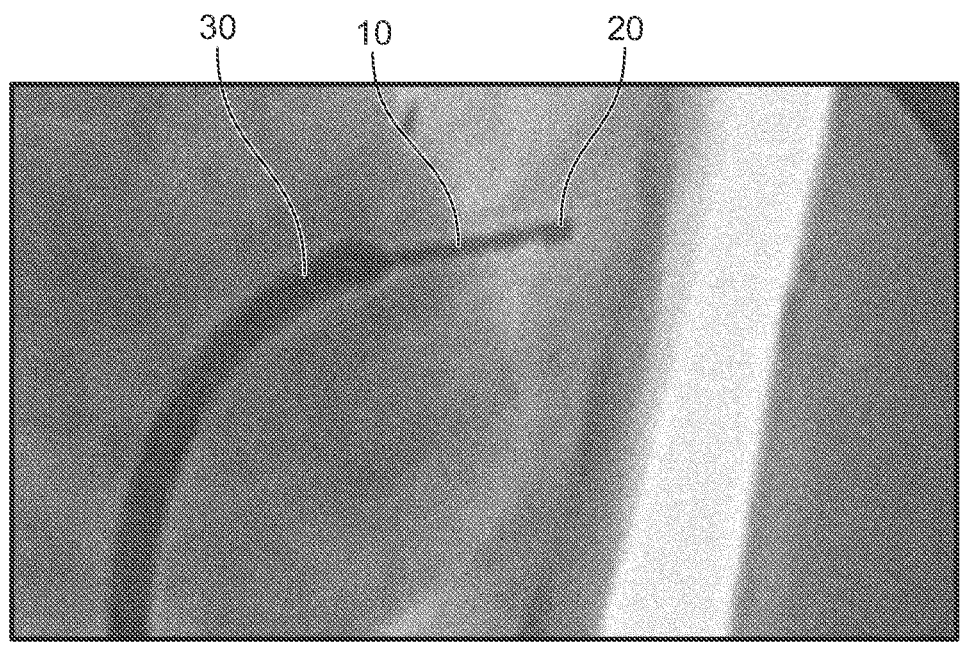
FIG. 2 is a representative fluoroscopic image corresponding to FIG. 1C showing the access sheath location.
Figure 3:
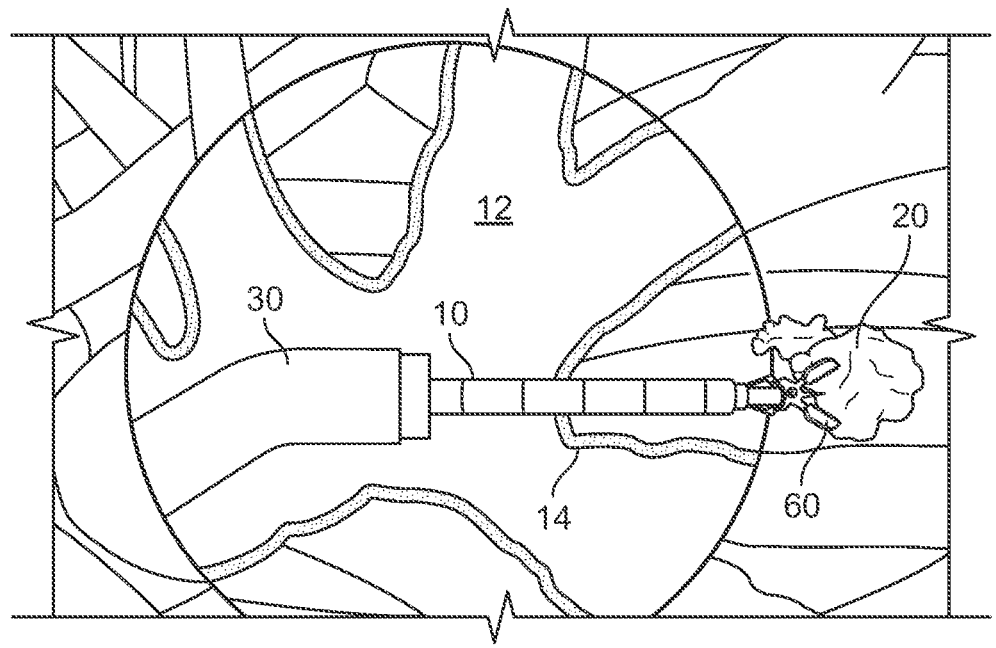
FIGS. 3, 4 illustrate carrying out a biopsy and ablation procedure on the region of interest through the access sheath, respectively.

FIGS. 1-3 sequentially illustrate a bronchoscopic-based technique for performing a medical procedure on a region of interest 20 located outside of the airway 12 in the lung parenchyma. The region of interest 20 may be spaced a distance from the airway from 3-40 mm, and in some cases, 10-15 mm. Examples of medical procedures include diagnostic and treatment type procedures including without limitation biopsy, ablation, seed placement, and local chemical agent delivery.

With reference first to FIG. 1A, a bronchoscope 30 is shown within airway 12, and in close proximity to airway wall 14. Access sheath 10 extends from the distal end of bronchoscope 30. The access sheath is close to, or perhaps in contact with, the airway wall 14. Needle 40 is advanced from the distal end of the access sheath 10 in the direction of the region of interest (ROI) 20, creating a hole through the airway wall 14.

FIG. 1B shows dilation member 50 inserted through pre-existing hole in the airway wall 14. Dilation member 50 is enlarged to expand the hole. In some instances, the hole is expanded by a factor of 2 to 4 (in some embodiments, about a factor of 3) more than the hole created by the needle. Dilation member 58 may be an inflatable balloon, expandable member, or another type of dilating member such as a tapered dilator.

FIG. 1C shows access sheath 10 advanced through the enlarged/dilated hole in the airway wall 14, and to the region of interest 20. Marker bands 18 are shown on the sheath to provide a visual indication of the depth of the sheath, or motion of the sheath. Marker bands may be ink, and evenly spaced axially along the sheath.

The region of interest is shown as a tissue mass such as a tumor. However, the region of interest may include others tissues, structures, or implants for which a procedure is desirable. It should be noted, however, that once the access catheter 10 is advanced beyond the airway 12, it is outside the view of the bronchoscope.

FIG. 2 shows a two dimensional fluoroscopic image view of the access sheath. Access sheath 10 is extending from bronchoscope 30, and towards the region of interest 20. The airways are not visible under the fluoroscopic view. The fluoroscopic view serves to track the access sheath and confirm the location of the instruments once the tools are outside of the airways, and outside the view of the bronchoscope.

FIG. 3 shows a biopsy forceps 60 extending from the distal end of the access sheath 10. The biopsy forceps 60 obtains a sample specimen from the region of interest.

Figure 4:
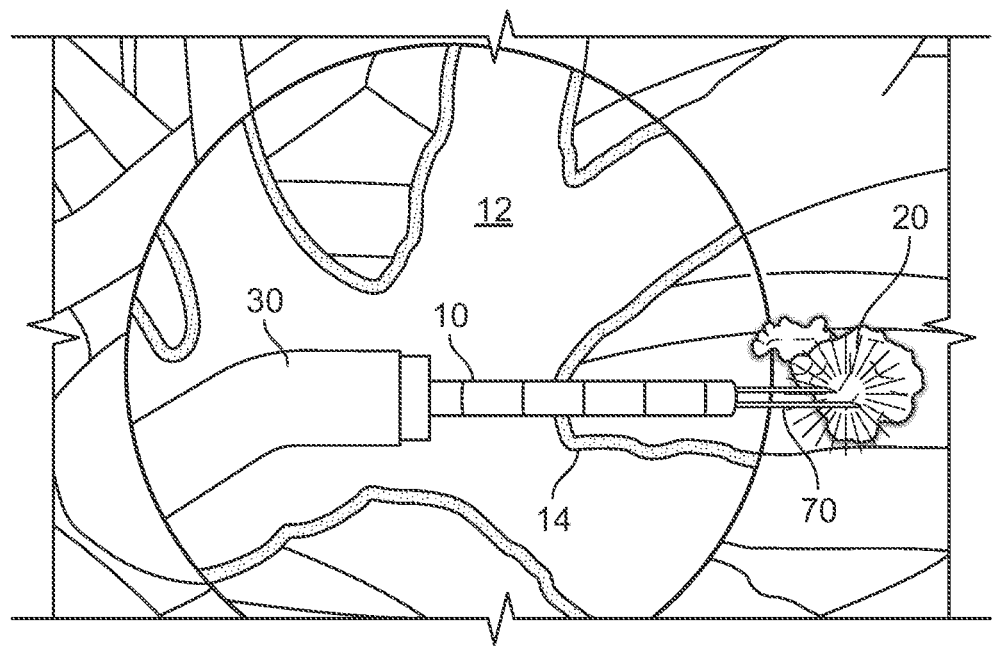

FIG. 4 shows ablation needles 70 extending from the distal end of the access sheath 10, and into the region of interest 20. The ablation needles 70 are activated to destroy the region of interest. Although forceps and ablation needles are shown, a wide range of tools may be delivered through the access sheath to carry out different types of medical procedures.

Electrosurgical Guide Wire

Figure 5A:
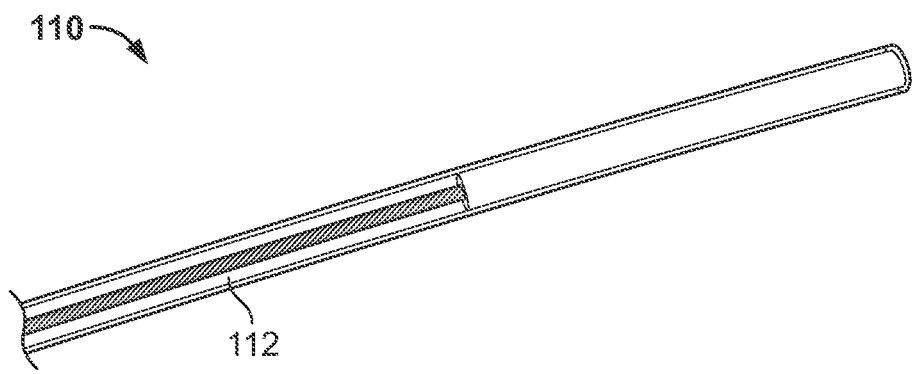
FIGS. 5A, 5B are partial perspective views of an electrosurgical stylet in a retracted and extended state respectively.
Figure 5B:
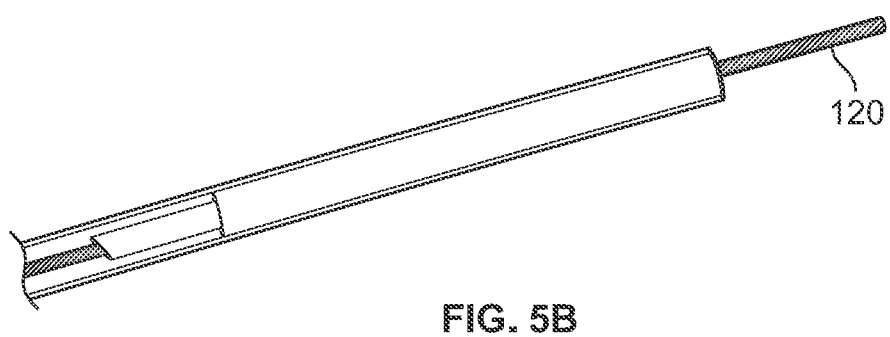

FIGS. 5A, 5B are partial perspective views of an electrosurgical stylet or guide member 110 in a retracted and extended state respectively.

The stylet 110 includes an outer cover 112, and inner member 120 axially movable relative to the cover. The distal section of the inner member terminates in an active electrode 120. The active electrode may be a wire with a blunted edge. In some embodiments, the wire may have a sharp tip whether beveled or otherwise. In other embodiments, the wire may have a rounded atraumatic ball or spherical shaped tip.

While in the retracted state shown in FIG. 5A, the stylet 100 is advanced through the working lumen of the bronchoscope, and into airway lumens. The outer cover 112 prevents the tip of the wire-shaped active electrode 120 from stabbing or damaging the bronchoscope or airway lumens.

The active electrode 120 is in electrical communication with a wire conductor (not shown) extending proximally, and coupled to an electrosurgical controller (not shown). Additionally, in embodiments, the active electrode 120 itself may be in the form of an elongate wire, and extend proximally to a detachable connector for coupling to the controller. Detachable connectors include, without limitation, removable plug-in type connectors. However, other types of connectors may be incorporated into the systems described herein to couple the guide member and active electrode to the controller.

The materials for the inner member 120 may vary widely. In embodiments, the inner member is formed of a metal or alloy. Examples of materials for the inner member include, without limitation, electrical conducting materials such as copper, stainless steel, Nitinol, and titanium.

The materials for the cover 112 may also vary. Examples of materials for the outer cover include, without limitation, extruded polymeric tubing formed of PEBAX, FEP, PTFE, PE, and Nylon.

Figure 6:
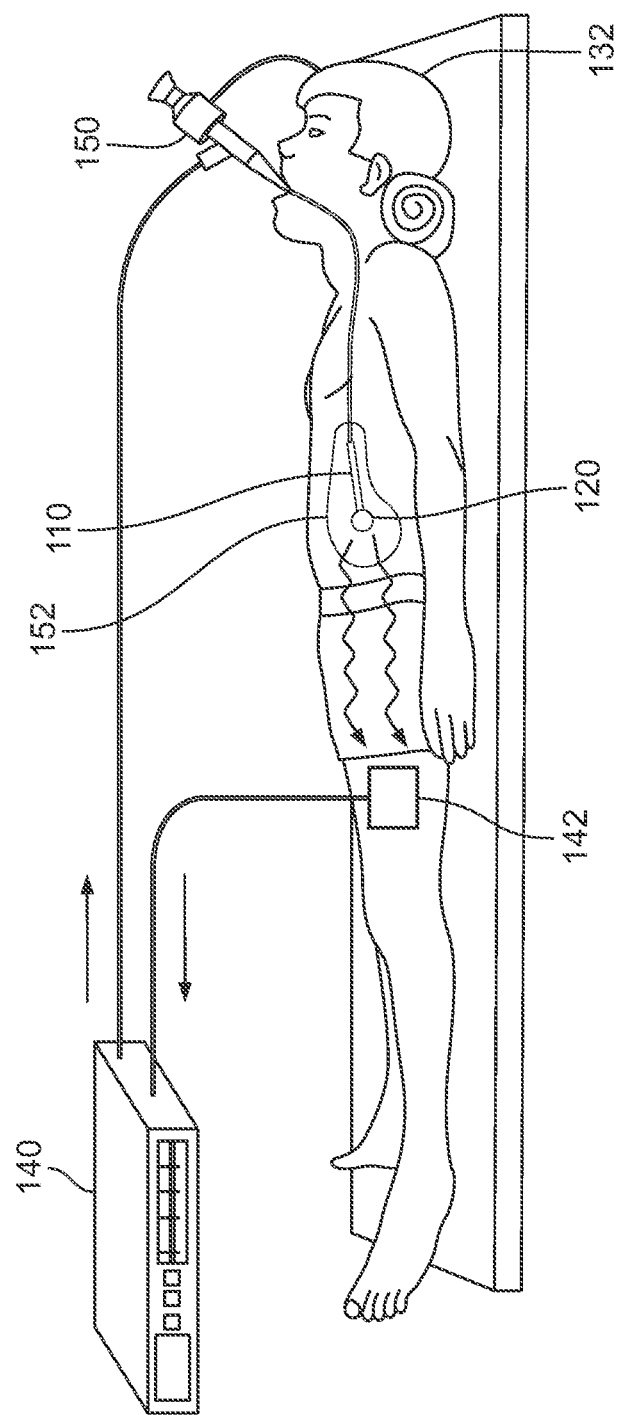
FIG. 6 is an illustration of a monopolar-based electrosurgical system.

With reference to FIG. 6, the guide member 110 is advanced from a bronchoscope 150 to a target position along an airway in the lung 152 of the patient 132. A controller 140 is shown electrically connected to the active electrode 120 and a dispersive electrode 142 affixed to the skin of the patient.

In embodiments, an alternating current (e.g., a RF current waveform) is applied to the circuit causing the active electrode to cut the target tissue in close vicinity of the active electrode. In embodiments, a sinusoidal voltage at a frequency of 400 kHz±100 kHz is applied. Power setting may vary from 5-300 watts. Timing for cutting may also vary. In embodiments, the energy is activated for the time required to cut (typically between 0.1 and 5 seconds; however, depending on the anatomy, tissue moisture content, salinity, and type (airway, parenchyma, tumor, etc.), cut times will vary. An example of a controller is the VIO 300D, manufactured by Erbe USA, Inc., Marietta, Ga. Examples of electrosurgical controllers for use with the electrosurgical instruments of the present invention are described in the literature including, without limitation, U.S. Pat. No. 5,599,344, US Patent Publication Nos. 20080249523, 20110190755, each of which is incorporated herein.

In addition to cutting, in embodiments, the controllers are operable to cauterize by application of a different energy setting typically referred to as the controller's coagulation mode. Providing a coagulation mode can add safety to the procedure by sealing small vessels that may be severed during a cutting procedure. Without intending to being bound to theory, coagulation is generally associated with a lower temperatures, modulated current, and higher voltages (up to 10,000 V peak to peak) to cause relatively deep tissue destruction than the cutting mode. Additionally, in embodiments the electrosurgical device is used a standalone product for performing electrocautery.

Figure 7A:
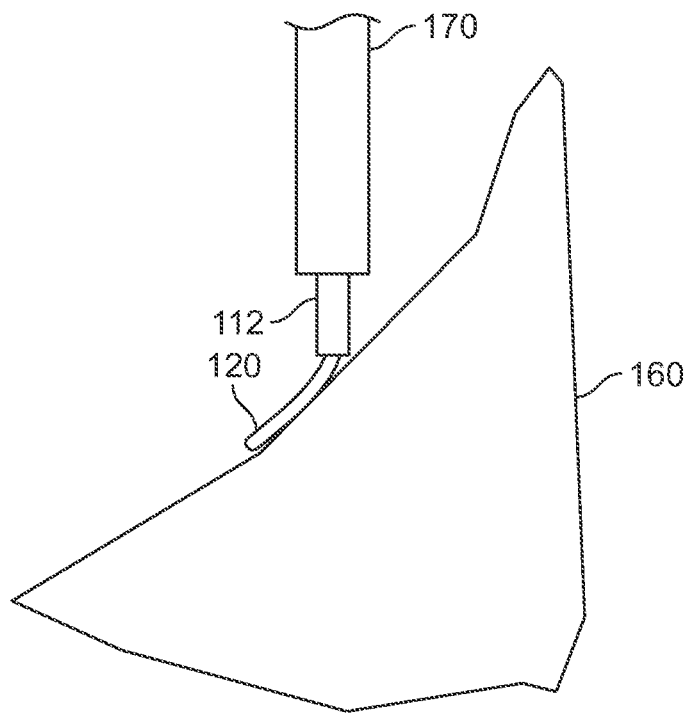
FIGS. 7A, 7B are sequential illustrations of an electrosurgical stylet being positioned and subsequently cutting the target tissue.

FIG. 7A illustrates the electrosurgical guide member described in FIGS. 5A, 5B, 6 cutting tissue 160. The active electrode 120 is advanced from the cover 112 and towards the airway wall. The active electrode 120 is further advanced against the tissue surface, conforming to the tissue surface. The active electrode is shown curving along the surface of the tissue such that a lateral surface of the electrode 120 is in contact with the tissue 160.

Figure 7B:
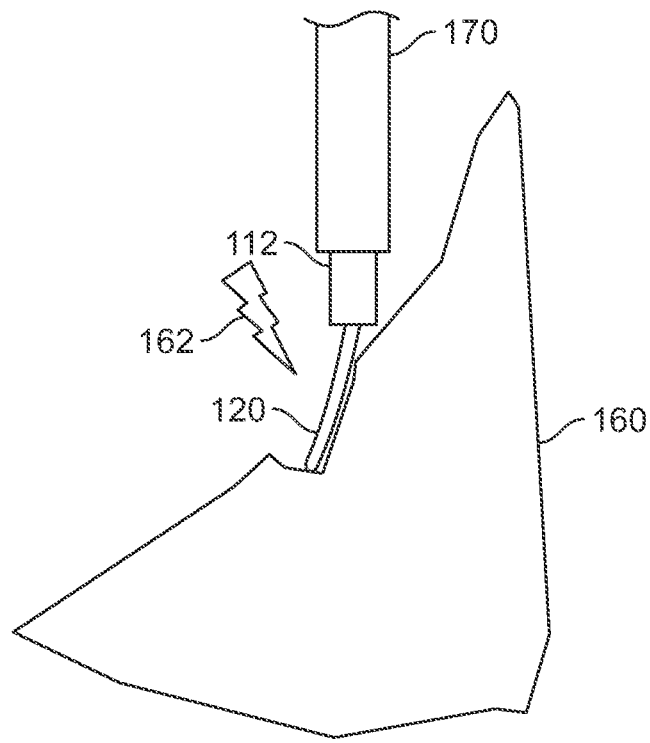

FIG. 7B shows application of energy 162 to the active electrode, cutting the tissue 160.

In the embodiment shown in FIG. 7B, the active electrode includes several cutting regions including a lateral circumferential region and the front end/edge. The length of lateral cutting area ranges from 1-20 mm. The tip has a diameter of 0.5 mm.

The multiple electrode cutting regions shown in the embodiment of FIG. 7B enable the physician to make larger holes than would be created if only the front edge region was active. Hole diameters corresponding to the embodiment shown in FIG. 7B are dependent upon the exposed electrode length 1 to 40 times larger than a hole created using only a wire tip, or front-only ablation.

After a hole, opening, or channel is created through the airway wall tissue 160, the wire 120 may be retracted into the guide member 112, and the guide member assembly exchanged for an access sheath 170. The guide sheath is advanced through the hole without the need to dilate the hole.

In alternative embodiments, the guide member assembly 110 is advanced beyond the airway wall and through parenchyma tissue to the ROI. Fluoroscopic guidance may be used to track the location of the guide member assembly outside of the airways.

After the guide member assembly reaches the target location, an access sheath 170 may be advanced over the guide member, through the pre-cut hole, and to the ROI (not shown). Advantageously, the access sheath 170 may be advanced to the ROI without the need for dilating the hole. Various medical procedures may be performed through the access sheath 170 as described herein.

Electrosurgical Guide Loop Electrode

Figure 8:
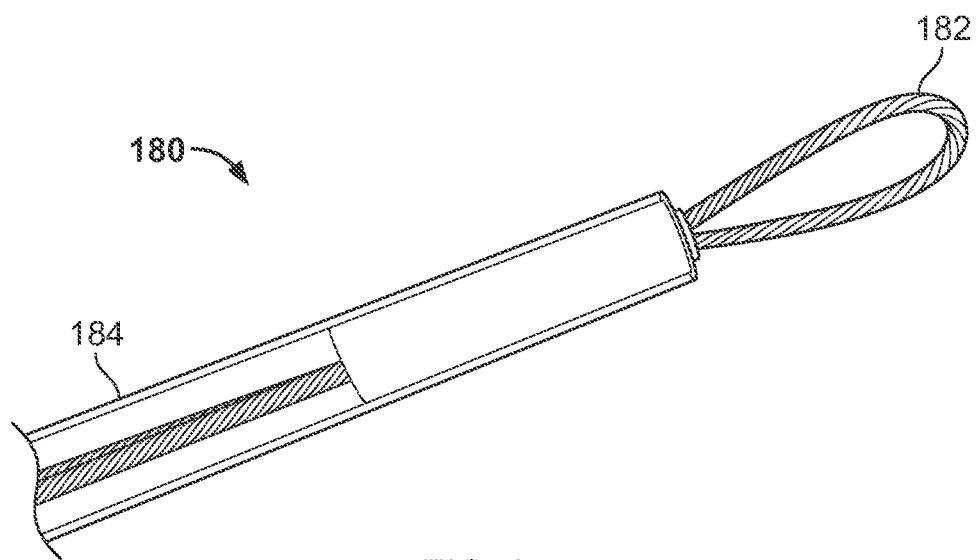
FIG. 8 is a partial perspective view of another electrosurgical instrument including a loop shaped electrode.

FIG. 8 is a partial perspective view of another electrosurgical guide instrument 180 including a loop shaped electrode 182. The loop electrode is shown protruding from an outer cover 184. The loop 182 and cover 184 may be made of similar materials to that used for the wire electrode member 120 and cover 112 shown and described in FIGS. 5A, 5B, respectively.

The width and length of the loop 182 preferably ranges from 1-3 mm and 2-10 mm, respectfully. Consequently, when activated, the loop electrode can make a relatively large cut through the airway wall. Additionally, because the loop electrode 182 naturally has a curved atraumatic shape, it may be advanced through the working lumen of a bronchoscope and airways without inadvertently piecing or damaging the lumen walls.

Once a hole has been created, the access sheaths described herein may be advanced through the surgically created hole to the ROI. The access sheath may be advanced into position over the loop guide instrument 180, or pushed into position with the loop instrument 180 previously removed. Using either technique, the access sheath is advanced through the hole without further dilation or enlargement of the hole.

Additionally, in embodiments, the inner wire 120 or loop members 182 may be configured to be actuatable from the proximal end of the device. Indeed, any of the active electrodes for cutting described herein may be configured to, or linked to, a handle or actuator assembly to extend and retract the active electrode from the sheaths. Various actuator mechanisms for use with the piercing members and electrodes are described herein.

Electrosurgical Access Sheath

Figure 9:
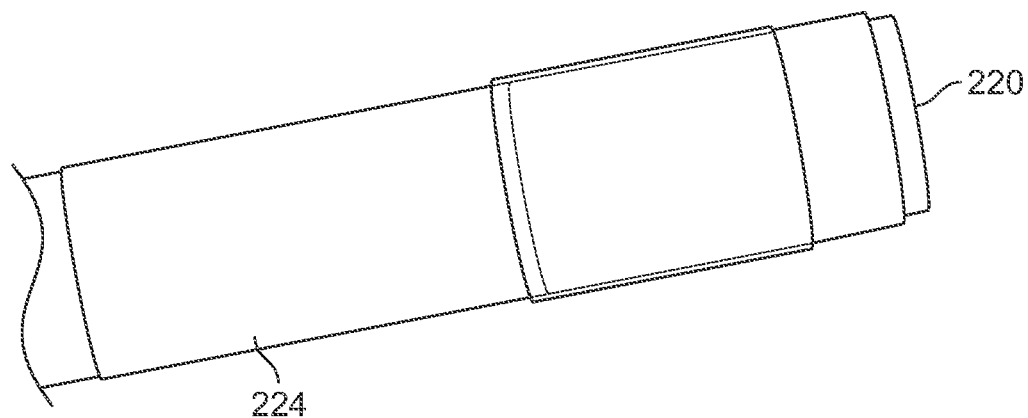
FIG. 9 is a partial perspective view of an access sheath including a ring shaped cutting electrode.

FIG. 9 is a partial perspective view of the distal section of another access sheath 210 including a ring shaped cutting electrode 220. The ring shaped electrode 220 protrudes from a tubular shaped body 224. An electrical conductor, braid, is in electrical contact with the electrode and extends proximally through the tubular body to the proximal section where the conductor is coupled to a controller.

Figure 10:
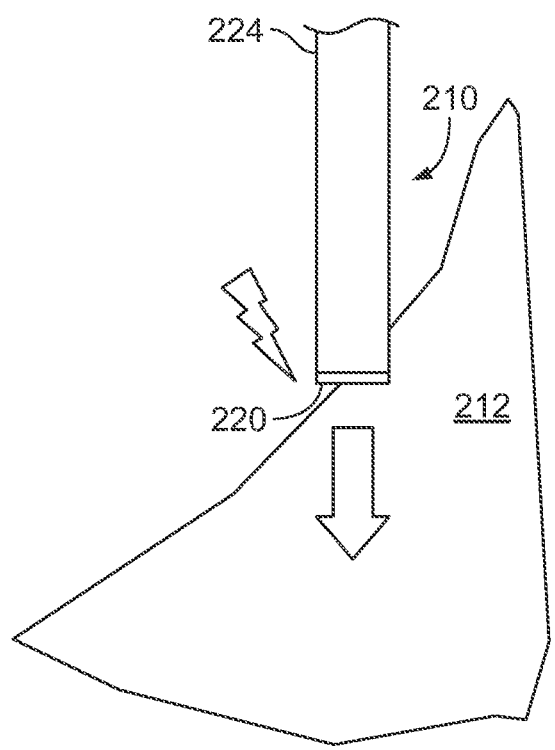
FIG. 10 is an illustration of the access sheath represented in FIG. 9 electrosurgically cutting tissue.

FIG. 10 illustrates the access sheath 210 cutting an opening through a tissue 212 when activated as described herein. The access sheath 210 is activated and advanced through the tissue, for example, the airway wall, creating a port through which the access sheath may be advanced.

Additionally, the access sheath is advanced through the hole without further dilation or enlargement of the hole. In embodiments, the outer diameter of the access sheath is approximately the same as the ring electrode. The outer diameter of the access sheath may range from 2 to 3 mm. The sheath diameter may be constant.

As described herein, the sheath and electrode are sized to accommodate procedural tools therethrough. In embodiments, the inner diameter of the electrode and sheath ranges from 1.8-2.8 mm. The electrode and sheath may be made of materials as described above in connection with the electrode 120 and outer cover 112 of FIGS. 5A, 5B. The electrode may be made of a platinum, iridium, stainless steel, tungsten, titanium, and other electrically conducting and x-ray visible materials for assisting the physician locate and track the instrument during a procedure. Further details of manufacturing the sheath 210 are described herein.

Figure 11A:
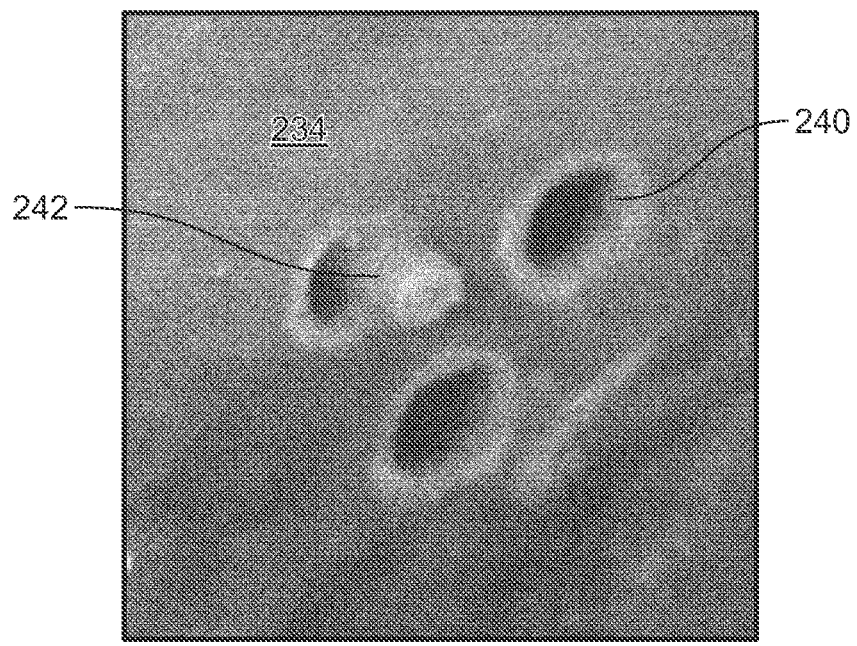
FIG. 11A is an illustration of several circular-shaped incisions created with an access sheath as shown in FIG. 9.
Figure 11B:
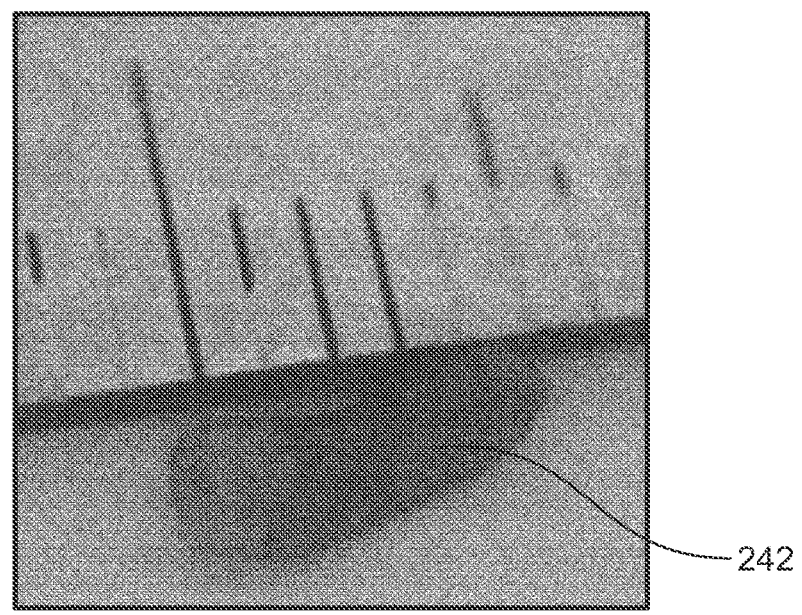
FIG. 11B is an illustration of a tissue plug captured from the access sheath represented in FIG. 9.

FIG. 11A is an illustration of several holes 240 in a tissue 234 made by the access sheath 210 described in FIG. 9. The tissue 234 is bovine liver. Power setting for cutting the holes ranged from 30 to 100 watts. The holes 240 are clearly defined, large (about 2 mm in diameter), and result in procuring or carving a tissue plug 242. The length of plug 242 with reference to FIG. 11B is about 5 mm of contiguous tissue.

Large sample biopsies are anticipated using the access sheath described herein. Evidence from sampling bovine liver described herein shows sample sizes as large as 20 mm long and 2 mm in diameter. In embodiments, a method and apparatus includes obtaining the tissue plugs described herein for use in minimally invasive mediastinoscopy where large sample size is highly desired. Additionally, biopsy sampling can be performed at other lymphatic sites and/or tumors.

Figure 12:
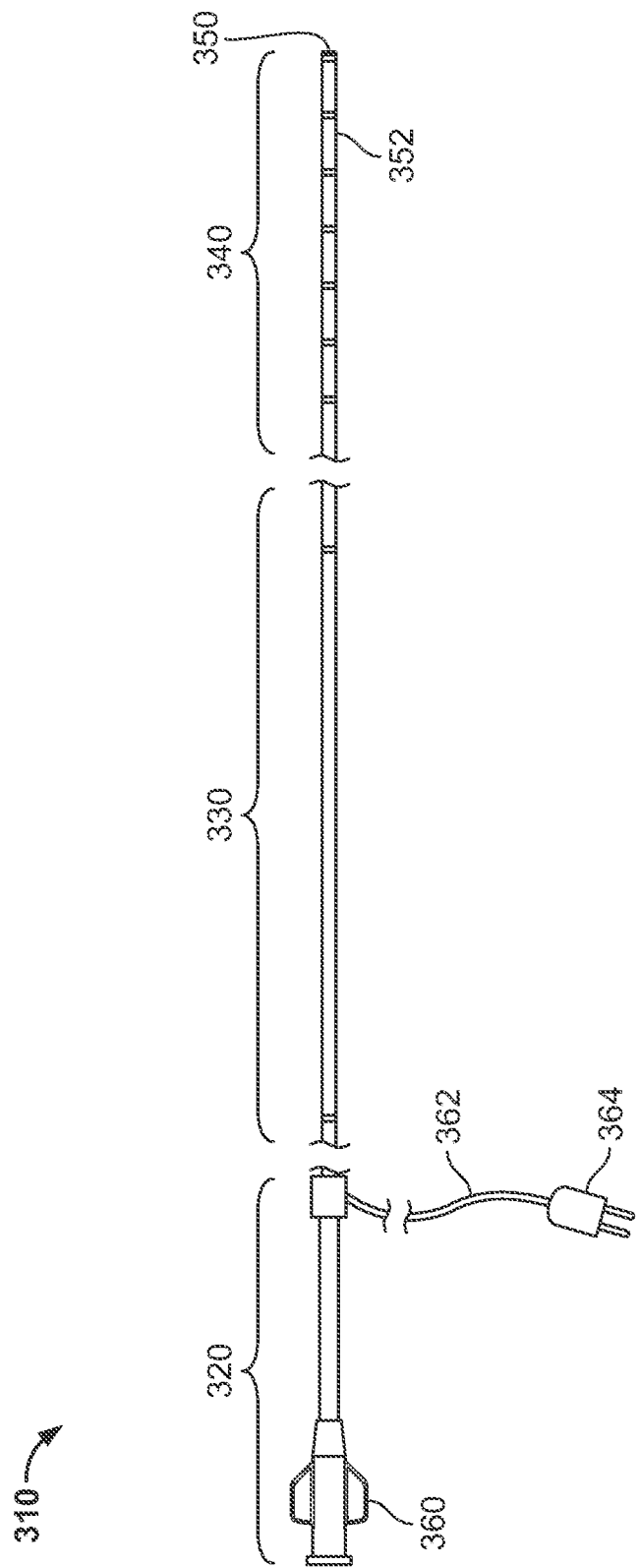
FIG. 12 is a side view of an electrosurgical access sheath.

FIG. 12 is a side view of an entire electrosurgical access sheath 310 in accordance with one embodiment of the invention. It includes a flexible tubular shaft having a proximal section 320, intermediate section 330, and distal section 340. As described above the tubular shaft is sized for various tools to be passed therethrough such as, without limitation, biopsy forceps, aspiration needles, electrosurgical and cryo-ablation catheters, snares, etc. The inner diameter of the tubular shaft may range from 1.8 to 2.8 mm, and preferably is about 2.0 mm. The outer diameter is less than 3 mm. In the embodiment shown in FIG. 12, the shaft intermediate and distal sections have a constant outer diameter.

Radiopaque markers 352 are shown in the form of bands evenly spaced along the distal section of the sheath. Bands 352 may be formed of various radiopaque materials including, for example, platinum, iridium, and other fluoroscopically opaque materials.

The proximal section 320 is shown having a hub 360 such as a Luer connector. Certain tools as described above may be advanced through the sheath, and conveniently connected with hub 360.

Electrical cable 362 is shown extending from the proximal section. Electrical cable terminates in a connector which may be detachably engaged with controller not shown. As will be described further herein, in embodiments, electrical cable 362 includes electrical conducting lines which are in electrical communication with the distal ring electrode 350 of the sheath.

The total length of the access sheath 310 may vary. In embodiments, the length from the hub 360 to the ring electrode 350 is about 35-45 inches preferably about 35-40 inches. In embodiments, the access sheath 310 has a total length suitable to be inserted through the working lumen of a bronchoscope in a patient, beyond the end of the bronchoscope tip, and to a remote or peripherally-located tissue growth or nodule. In embodiments, the nodules and ROIs may be located in the parenchyma tissue outside of the airways 3 to 100 mm from the end of the scope, or from the wall of the airway.

Figure 13:
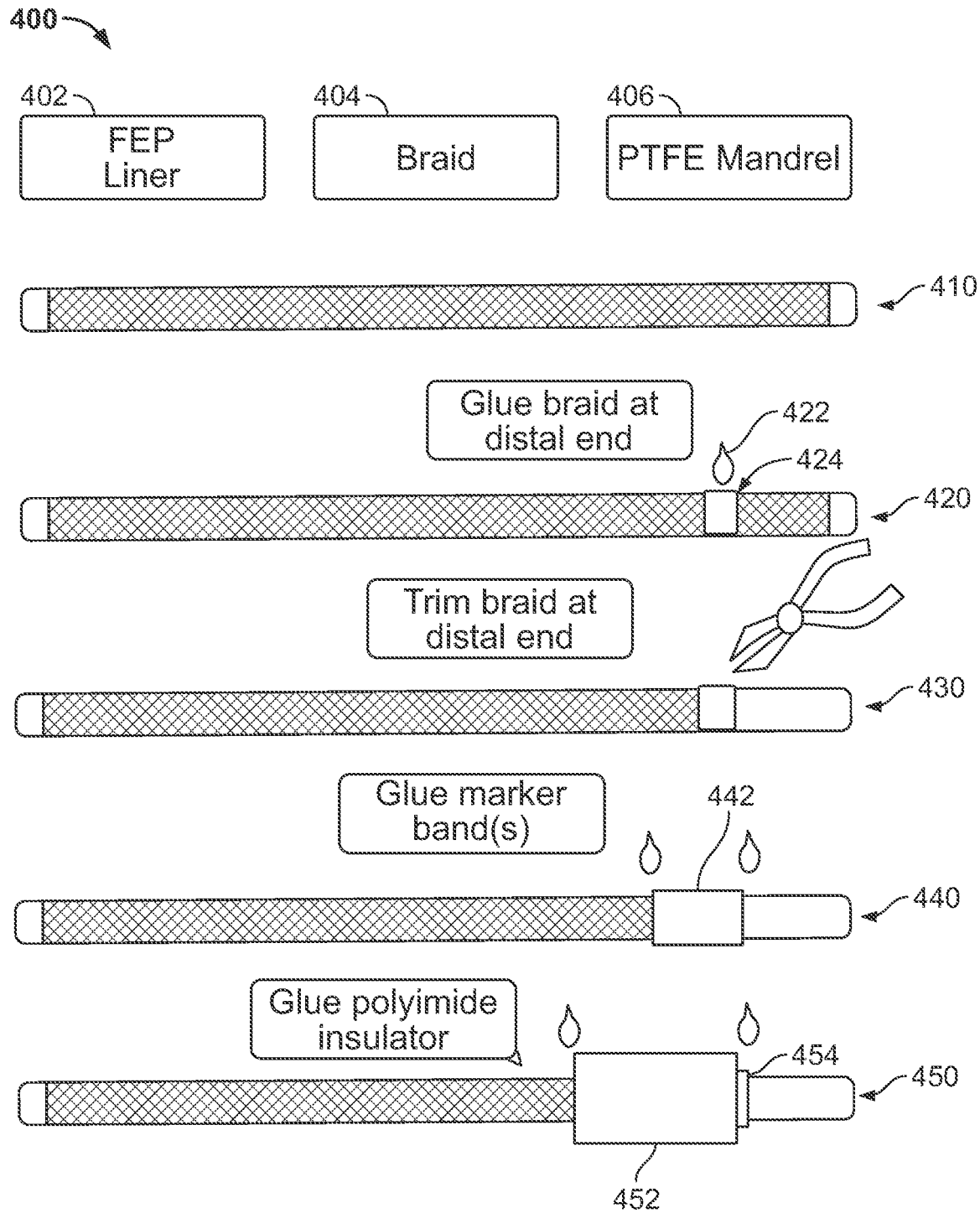
FIGS. 13, 14 illustrate sequentially steps to manufacture an electrosurgical access sheath.
Figure 14:
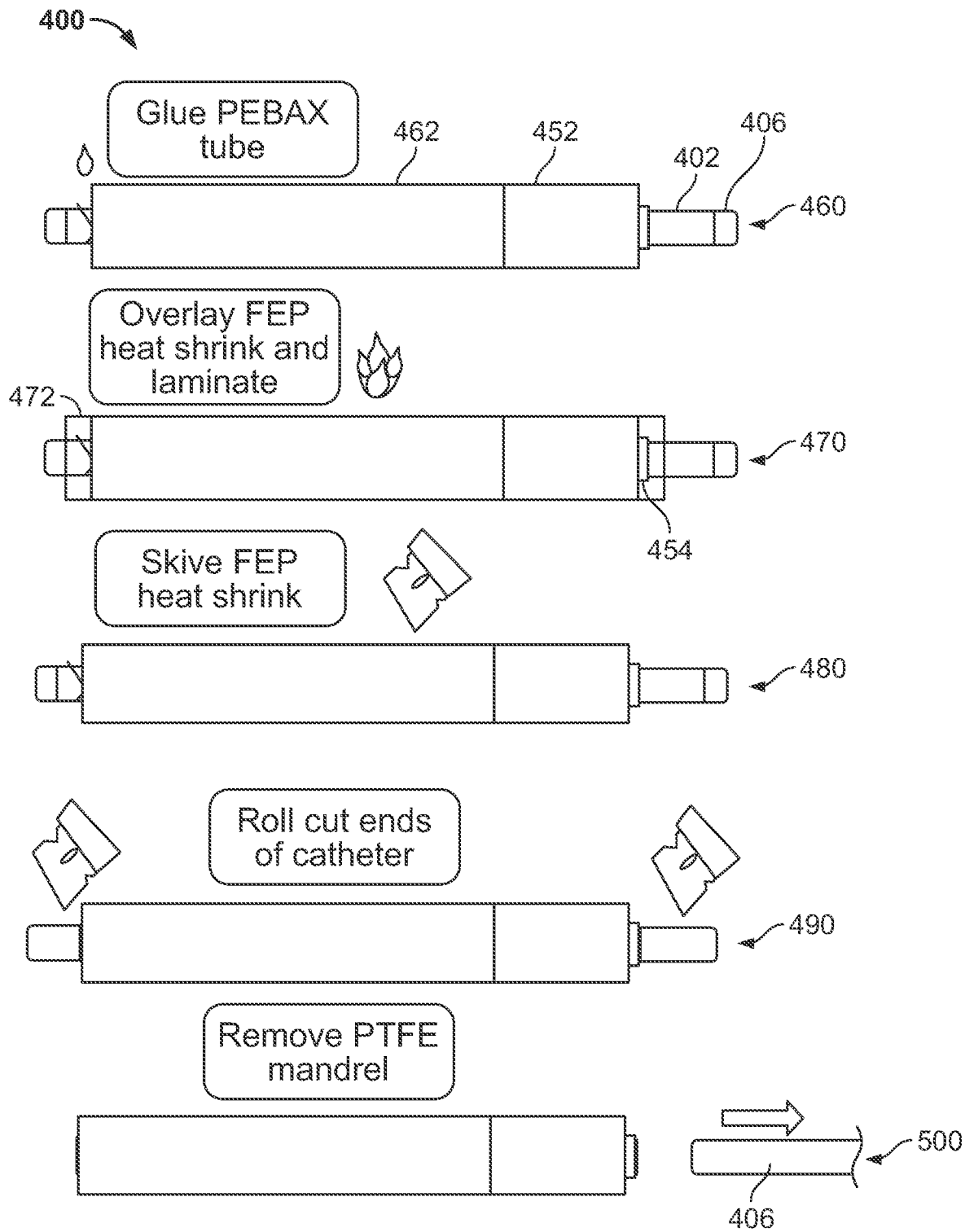

FIGS. 13, 14 illustrate a process 400 to manufacture an electrosurgical access sheath in accordance with embodiments of the invention.

Initially, with reference to step 410, a fluorinated ethylene-propylene (FEP) liner 402 is shown surrounding a polytetrafluoroethylene (PTFE) mandrel having an outer diameter of about 2 mm. A braid 404 is shown surrounding the liner 402.

The pitch of the braid may range from 20 to 100 PPI. Additionally, the flexibility of the sheath may be varied by changes to the braid pitch (e.g. tight or loose pitch, the braid to coil transition(s), and the thickness of the braiding material). A preferred braid configuration would be a 16 spool woven construct of 0.001"×0.003" flat wire, from stainless steel, with a pick count of 48 PPI. Additionally, in embodiments, the braid is made of an electrical conducting material and serves as the electrical conductor between the controller and the active electrode.

Step 420 illustrates bonding the braid 404 to the liner 402 at the distal end 424. Bonding may be carried out, e.g., using various adhesives 422.

Step 430 illustrates trimming the braid at the distal end of the sheath.

Step 440 illustrates fastening an elongated tubular metal electrode 442 to the braid 404 and liner 406. The tubular metal electrode is shown being glued in place.

Step 450 illustrates covering the proximal region of the metal electrode 442 with an insulator 452, thereby defining a ring-shaped electrode 454.

The insulator serves to protect the active electrode from damaging other parts of the sheath in the vicinity of the active electrode. Exemplary materials for the insulator include without limitation polyimide, fluoropolymer, PEEK, aluminum oxide (alumina), and parylene.

Step 460 illustrates a polymer tubing 462 bonded over the braid/liner. Exemplary materials for the polymer tubing may be PEBAX. The polymer tubing 462 may be bonded with, e.g., glue.

Step 470 illustrates an outer layer 472 of FEP surrounding the polymer tubing 462, insulator 452, and ring electrode 454. The outer layer of FEP is heat-shrunk in place.

Step 480 illustrates trimming (e.g., skive off) the FEP layer, to expose the laminated polymer tubing 462.

Step 490 illustrates trimming (e.g., roll cutting) the inner FEP liner 402 and excess braid.

Step 500 shows removing the mandrel 406, and completing the build of the shaft of the electrosurgical access sheath.

Additionally, an electrical cable (e.g., the cable 362 shown in FIG. 12) is installed to the access sheath. In embodiments, the proximal section of the access sheath is skived or trimmed to expose a portion of the metal braid. The electrical cable is joined at a joint to the exposed braid. Then, another outer layer or electrical insulation is applied to the joint to electrically isolate and strengthen the joint.

Additionally, the electrical conductor extending through the access sheath from the controller to the active electrode may vary. In embodiments, the configuration of the electrical conductor is a braid as described above. In another embodiment, the electrical conductor is a separate insulated cable extending through the tubular shaft and fixed in position. In another embodiment, the electrical conductor is a separate axially movable component (e.g. stylet) that passes through the lumen of the sheath and couples with the active electrode at the distal end. Indeed, the electrical conductor may have a wide variety of configurations.

FIGS. 15A, 15B are partial side and cross sectional views respectively of another electrosurgical access sheath 510. The electrosurgical access sheath 510 is similar to that described above in connection with FIG. 9. Sheath includes a large distal active electrode 512 and a large tubular shaft 514 for tools to be advanced therethrough. However, the shape of the electrode is different than that shown in FIG. 9. The cross-sectional shape of the active electrode 512 shown in FIGS. 15A-15B is C-shaped. The materials and fabrication may otherwise be similar to that described herein.

FIG. 15C is a partial perspective view of the electrosurgical access sheath 510 shown in FIGS. 15A, 15B.

Although a number of specific shapes are described herein, the cross-sectional shape of the active electrode may vary widely. The shape may be circular or non-circular. The shape may protrude from the end of the access sheath and include only a front edge and little or no lateral surface for cutting. The electrode may take a form somewhat analogous to a cookie-cutter type stencil or die for cutting through substrates such as, e.g., thin airway walls. Plugs of different shapes corresponding to the cutter are carved including circles, gunsight, stars, bulls-eye, triangles, squares, and other geometries. The shapes may be formed as a group of discrete slits, or one contiguous pattern.

Additionally, electrode geometry corresponding to cross or perpendicular hatches may be incorporated into the basic shape. Cross hatches may be added to, e.g., a circle. Hatches may be perpendicular to the circle and radially oriented.

Non-limiting preferable characteristic cross dimensions for the die (e.g., diameter or length, or height) are in the range of a 1.5-3 mm.

Figure 16:
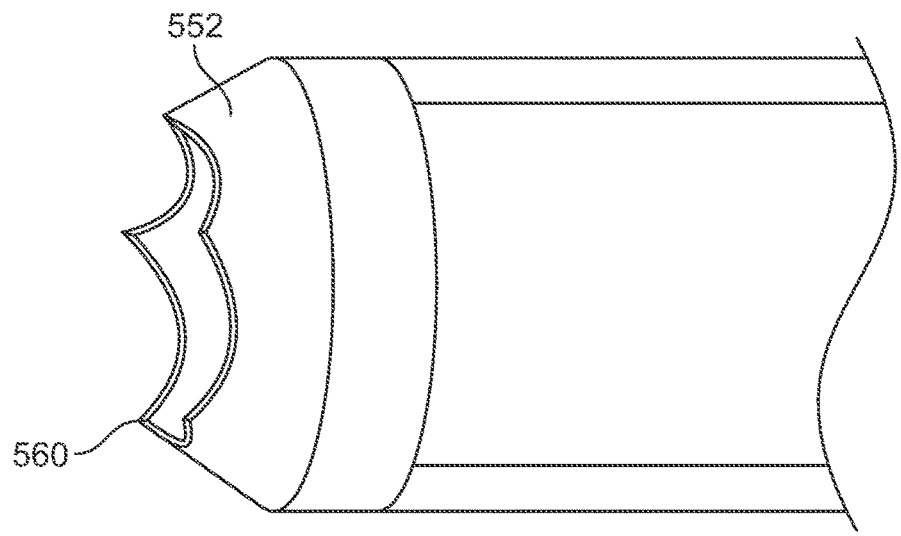
FIG. 16 is an illustration of another electrosurgical access sheath.

FIG. 16 shows an active electrode 552 having pointed or sharp features 562 to aid in cutting and to reduce the penetration force. The active electrode 552 in FIG. 16 includes tines 562.

Figure 17A:
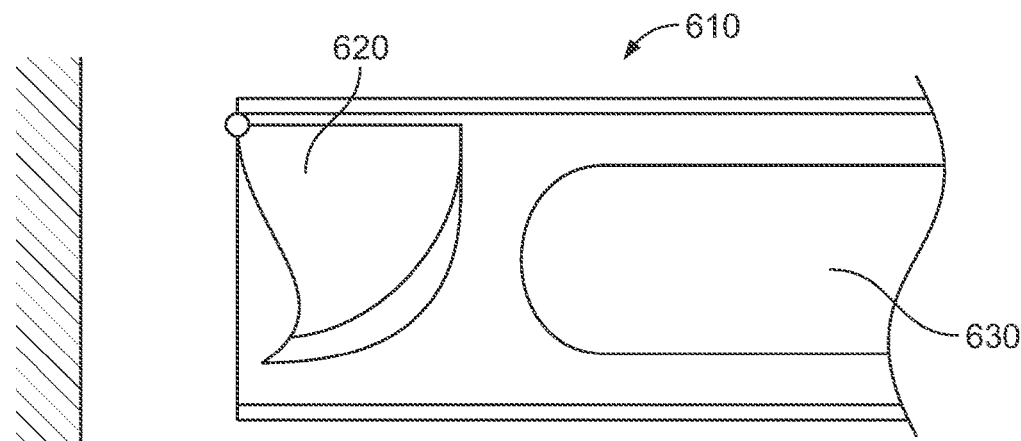
FIGS. 17A, 17B are illustrations of another electrosurgical access sheath having a retracted and extended state respectively.
Figure 17B:
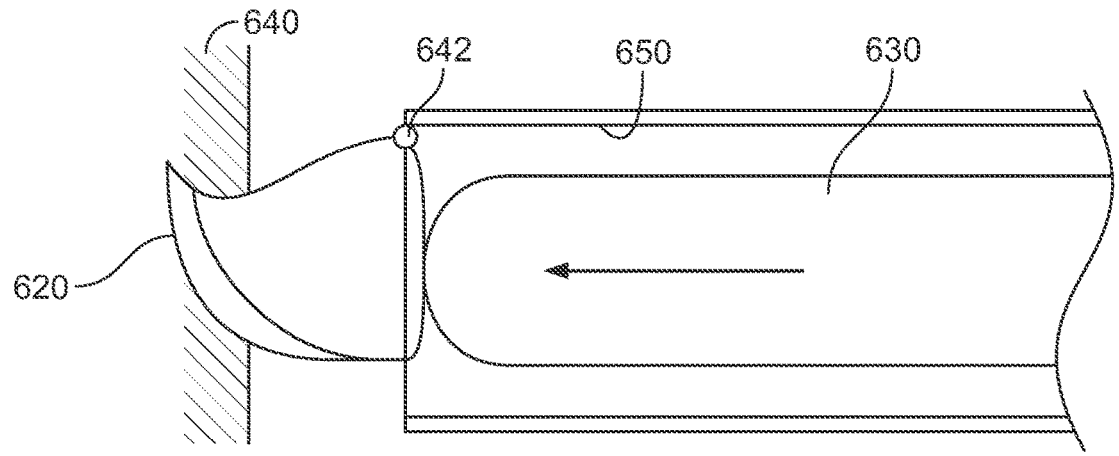

FIGS. 17A, 17B are illustrations of another electrosurgical access sheath 610 having a cutting member 620 in a retracted and extended state respectively.

FIG. 17B shows the cutting member 620 urged by stylet pusher 630 into the tissue 640. The cutting member 620 is shown pivoting from a retracted position into an extended position about axis 642. Additionally, during actuation, pusher may deliver electrical waveforms to enable the cutting member to electrosurgically cut through the tissue 640. In alternative embodiments, the pusher configuration and cutting is purely mechanical.

Subsequent to cutting the hole through the tissue 640, the sheath 610 may be advanced towards the ROI (not shown). With the cutting member 642 fully rotated out of the lumen 650 (not shown), the pusher 630 may be exchanged with one or more ancillary tools to carry out an ancillary medical procedure on the ROI.

Figure 18A:
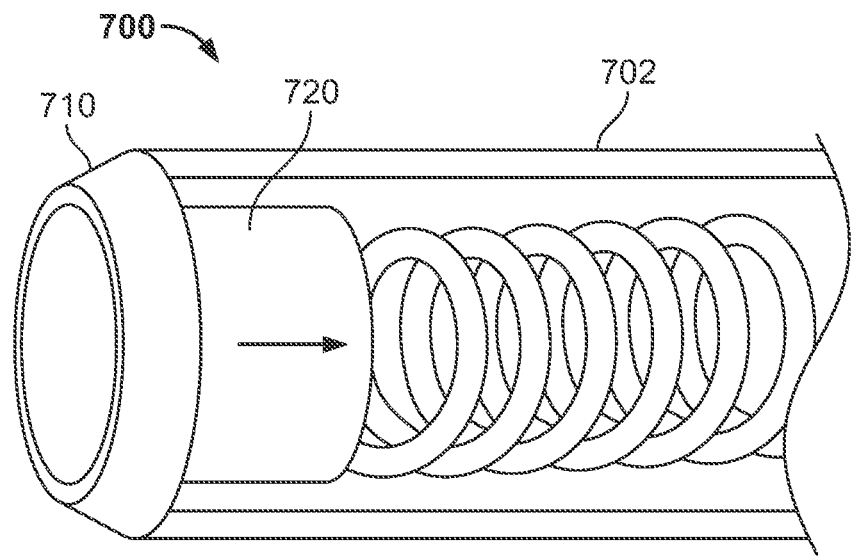
FIGS. 18A, 18B are illustrations of another electrosurgical access sheath having a cutting annulus in an exposed and neutralized state respectively.
Figure 18B:
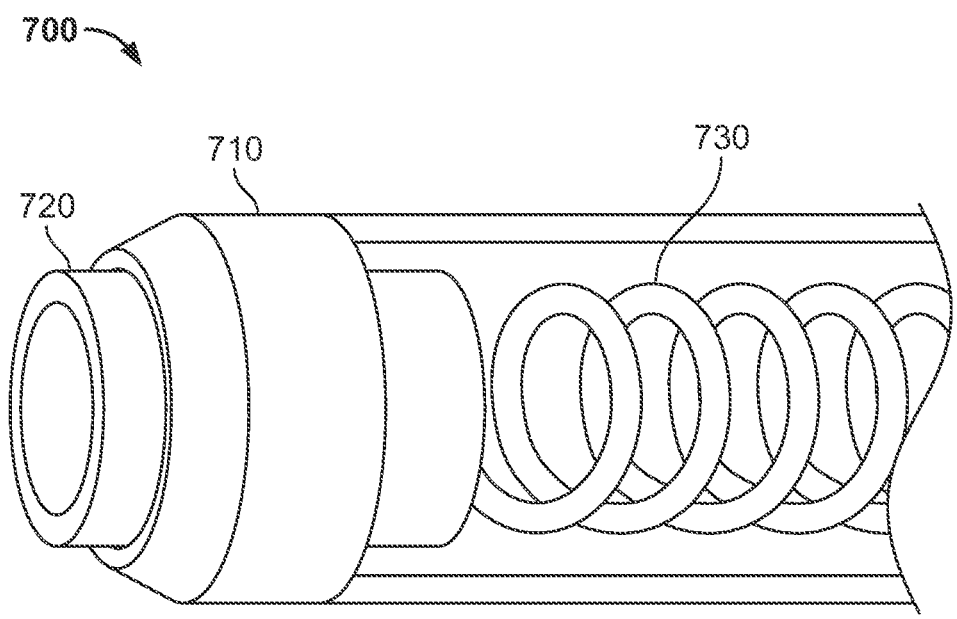

FIGS. 18A, 18B are partial illustrations of another electrosurgical access sheath 700 having another type of cutter 710 in an exposed and neutralized state respectively.

In FIG. 18A, the cutting member 710 is shown bare or exposed. It has an annular tip. The cutting member 710 may have, e.g., the shape of a coring needle.

A protective end 720 in the shape of a cylinder is shown retracted or withdrawn in elongate tube 702.

FIG. 18B illustrates the protective end 720 extended from the cutting tip 710, preventing or neutralizing the cutting action.

The actuation between the cutting tip 710 and protective cylinder 720 may be carried out by displacing one member or the other. The protective end 720, may be, for example, biased to extend beyond the cutting member via a spring 730. However, other actuating mechanisms may be employed including pull wires, and more sophisticated actuating elements.

Additionally, the cutting member and or protective cylinder may be utilized as an active electrode to facilitate cutting.

After the hole is created, ancillary tools may be advanced through the lumen of the shaft 702 as described herein.

Although a number of embodiments have been disclosed above, it is to be understood that other modifications and variations can be made to the disclosed embodiments without departing from the subject invention.

The invention claimed is:

1. A minimally invasive surgical method for assisting a physician perform an ancillary surgical procedure on a region of interest (ROI) in a lung of a patient, the method comprising:

providing an access catheter comprising a flexible proximal section and a distal end comprising an active electrode, the access catheter further comprising a passageway extending from the proximal section to the distal end;

advancing the distal end of the access catheter through the airways of the patient and to a target site along an airway wall;

activating the active electrode while advancing the distal end of the access catheter into the airway wall at the target site, thereby creating an opening and capturing a cylindrical-shaped tissue plug;

advancing the distal end of the access catheter through the opening an estimated distance beyond the airway wall, through the lung parenchyma and to the ROI;

ejecting the tissue plug into the parenchyma of the lung; and performing the ancillary surgical procedure on the ROI with an ancillary instrument through the passageway of the access catheter.

2. The method of claim 1, further comprising computing the estimated distance along a predetermined path on a computer processor.

3. The method of claim 2, wherein the path is based on pre-acquired image data, and a physician's identification of an ROI in the image data.

4. The method of claim 1, wherein the ancillary surgical procedure is a tissue ablation procedure.

5. The method of claim 1, wherein the ancillary surgical procedure is a biopsy procedure.

6. The method of claim 1, wherein the active electrode is ring-shaped.

7. The method of claim 6, wherein the passageway and ring-shaped active electrode comprise an inner diameter of at least 2 mm.

8. The method of claim 7, wherein the active electrode has an uncovered portion less than 1 mm in length.

9. The method of claim 1, further comprising applying a sinusoidal voltage waveform from the active electrode at a frequency between 300 kHz and 500 kHz.

* * * * *